(12) United States Patent
Kinsella

(10) Patent No.: US 9,845,512 B2
(45) Date of Patent: Dec. 19, 2017

(54) SCREENING ASSAY EMPLOYING DEX AND GDF8

(75) Inventor: Todd M. Kinsella, Redwood City, CA (US)

(73) Assignee: RIGEL PHARMACEUTICALS, INC., South San Francisco, CA (US)

( * ) Notice: Subject to any disclaimer, the term of this patent is extended or adjusted under 35 U.S.C. 154(b) by 571 days.

(21) Appl. No.: 12/985,232

(22) Filed: Jan. 5, 2011

(65) Prior Publication Data

US 2011/0177001 A1 Jul. 21, 2011

Related U.S. Application Data

(60) Provisional application No. 61/295,631, filed on Jan. 15, 2010.

(51) Int. Cl.

| C12Q 1/68 | (2006.01) |
| A61K 31/573 | (2006.01) |
| A61K 38/18 | (2006.01) |
| C12N 5/10 | (2006.01) |
| A61K 49/00 | (2006.01) |
| A61K 45/06 | (2006.01) |

(52) U.S. Cl.
CPC .......... *C12Q 1/6897* (2013.01); *A61K 31/573* (2013.01); *A61K 38/1841* (2013.01); *A61K 45/06* (2013.01); *G01N 2333/71* (2013.01); *G01N 2333/723* (2013.01); *G01N 2500/10* (2013.01)

(58) Field of Classification Search
None
See application file for complete search history.

(56) References Cited

U.S. PATENT DOCUMENTS

| 2005/0014733 | A1 | 1/2005 | Whittemore et al. |
| 2006/0069049 | A1 | 3/2006 | Goldberg et al. |
| 2007/0149577 | A1 | 6/2007 | Hamilton et al. |
| 2007/0281928 | A1 | 12/2007 | Clark et al. |
| 2007/0281959 | A1 | 12/2007 | Zhi |
| 2008/0076795 | A1 | 3/2008 | Ali et al. |
| 2008/0090792 | A1 | 4/2008 | Barr et al. |
| 2009/0074675 | A1 | 3/2009 | Eldred et al. |
| 2009/0075995 | A1 | 3/2009 | Weinstein et al. |
| 2009/0105292 | A9 | 4/2009 | Zhi et al. |
| 2009/0137655 | A1 | 5/2009 | Scanlan et al. |
| 2009/0170898 | A1 | 7/2009 | Bengtsson et al. |
| 2009/0227548 | A1 | 9/2009 | Glossop et al. |
| 2009/0291928 | A1 | 11/2009 | Nishitani et al. |
| 2013/0065820 | A1* | 3/2013 | Bower et al. ........... 514/4.8 |

FOREIGN PATENT DOCUMENTS

| WO | WO9956768 | 11/1999 |
| WO | WO02061046 | 8/2002 |

OTHER PUBLICATIONS

Miner et al., Mol. Endocrinol., 2003, 17(1):117-127.*
Jager et al., J. Orthop. Res., 2008, vol. 26(1):1440-1448 (Abstract).*
Cheng et al., J. Biol. Chem., 2008, vol. 283(21):14665-14673.*
Kirsch et al., EMBO J., 2000, 19(13):3314-3324.*
Jager et al., J. Orthop. Res., 2008, vol. 26(1):1440-1448.*
Higashibata et al., J. Bone Miner. Res., 2004, vol. 19(1):78-88.*
Paliwal et al., Aging, 2012, vol. 4(8):553-566.*
PCT/US11/20266, International Search Report and Written Opinion, dated Mar. 29, 2011, 8pgs.
Bodine, et al., "Identification of ubiquitin ligases required for skeletal muscle atrophy", Science, 2001, 294:1704-8.
Bodine, et al., "Identification of ubiquitin ligases required for skeletal muscle atrophy", Supplementary Material, Science, 2001, 294, 9pgs.
Crepaldi, et al., "Conditional activation of MET in differentiated skeletal muscle induces atrophy", J Biol Chem., 2007, 282:6812-22.
Dogra, et al., "TNF-related weak inducer of apoptosis (TWEAK) is a potent skeletal muscle-wasting cytokine", FASEB J., 2007, 21:1857-69.
Gilson, et al., "Myostatin gene deletion prevents glucocorticoid-induced muscle atrophy", Endocrinology, 2007, 148:452-60.
Jackman, et al., "The molecular basis of skeletal muscle atrophy", Am J Physiol Cell Physiol., 2004, 287:C834-43.
Koncarevic, et al., "The ubiquitin-protein ligase Nedd4 targets Notch1 in skeletal muscle and distinguishes the subset of atrophies caused by reduced muscle tension", FASEB J., 2007, 21:427-37.
Li, et al., "Atrogin-1/muscle atrophy F-box inhibits calcineurin-dependent cardiac hypertrophy by participating in an SCF ubiquitin ligase complex", J Clin Invest., 2004, 114:1058-71.
Li, et al., "TNF-alpha acts via p38 MAPK to stimulate expression of the ubiquitin ligase atroginl/MAFbx in skeletal muscle", FASEB J., 2005, 19:362-70.
Ma, et al., "Characterization of 5'-regulatory region of human myostatin gene: regulation by dexamethasone in vitro", Am J Physiol Endocrinol Metab., 2001, 281:E1128-36.
Ma, et al., "Glucocorticoid-induced skeletal muscle atrophy is associated with upregulation of myostatin gene expression", Am J Physiol Endocrinol Metab., 2003, 285:E363-71.
Salehian, et al., "The effect of glutamine on prevention of glucocorticoid-induced skeletal muscle atrophy is associated with myostatin suppression", Metab., 2006, 55:1239-47.
Schakman, et al., "Mechanisms of glucocorticoid-induced myopathy", J Endocrinol, 2008, 197:1-10.
Waddell, et al., "The glucocorticoid receptor and FOXO1 synergistically activate the skeletal muscle atrophy-associated MuRF1 gene", Am J Physiol Endocrinol Metab., 2008, 295:E785-97.

(Continued)

*Primary Examiner* — Xiaozhen Xie
(74) *Attorney, Agent, or Firm* — James S. Keddie; Carol L. Francis; Travis Young

(57) ABSTRACT

Certain aspects of this disclosure relate to a method that comprises contacting a mammalian cell with a glucocorticoid receptor ligand and a myostatin receptor ligand, thereby activating the glucocorticoid receptor and said myostatin receptor. A screening assay employing the same is also provided.

20 Claims, 2 Drawing Sheets

(56) References Cited

OTHER PUBLICATIONS

Sandri, Marco, et al., "Foxo Transcription Factors Induce the Atrophy-Related Ubiquitin Ligase Atrogin-1 and Cause Skeletal Muscle Atrophy", Cell,117:399-412, 2004.
Communication and Supplementary European Search Report for European application No. 11733207.2, dated Jul. 15, 2013, 5 pages.

* cited by examiner

SCREENING ASSAY EMPLOYING DEX AND GDF8

CROSS-REFERENCING

This patent application claims the benefit of U.S. provisional patent application Ser. No. 61/295,631, filed on Jan. 15, 2010, which application is incorporated by reference herein in its entirety.

BACKGROUND

A general loss of muscle mass or atrophy is a characteristic response to fasting, as well as many diseases, including advanced cancer, renal failure, sepsis, cachexia, arthritis, osteoporosis, and diabetes. Atrophy of muscles also results from their disuse or denervation, e.g., immobilization, muscle unloading, spinal cord injury etc., and atrophy contributes substantially to many common health problems, including but not limited to HIV, chronic heart failure, chronic kidney disease, liver cirrhosis, burn injuries, osteoporosis, arthritis etc. Regardless of the cause of muscle atrophy, skeletal muscle atrophy is characterized by a decrease in protein content, fiber diameter, force production, and fatigue resistance.

Loss of muscle mass associated with progression of atrophy has been studied in animals subjected to denervation, immobilization, starvation, and animals implanted with cancer cells capable of inducing muscle wasting. Alternatively, atrophy can be induced in animals subjected to glucocorticoid administration. In these animals, the degree of muscle wasting can be assessed by employing a variety of measurements that record changes in muscle weights or fiber cross sectional area, and by performing kinetic experiments using a large number of animals etc. Detecting a significant change in muscle mass or in kinetics often requires a long waiting period. Measurement of muscle weight and fiber cross sectional area require cumbersome surgical procedures, cross-sectional area measurements and often the animal is sacrificed. Thus, such procedures usually require a large number of animals and precludes being able to follow a set of muscles, temporally, in the same animal.

Certain aspects of this disclosure relate to a method for inducing an atrophy response.

SUMMARY

Certain aspects of this disclosure relate to a method that comprises contacting a mammalian cell with a glucocorticoid receptor ligand and a myostatin receptor ligand, thereby activating the glucocorticoid receptor and the myostatin receptor. Screening assays involving the same are also provided.

In one embodiment a method comprising contacting a mammalian cell with a glucocorticoid receptor ligand a myostatin receptor ligand, thereby activating the glucocorticoid receptor and the myostatin receptor, is provided. In certain cases, the contacting initiates an atrophy response by the mammalian cell.

In certain embodiments, the contacting may done by administering the glucocorticoid receptor ligand and myostatin receptor ligand to a mammal (i.e., in vivo). In other embodiments, the contacting may be done by contacting the glucocorticoid receptor ligand and myostatin receptor ligand with a cultured cell in vitro, e.g., a cultured muscle cell.

In particular embodiments, the glucocorticoid receptor ligand may be contacted with the mammalian cell at a concentration in the range of 0.1 µM to 100 µM, and the myostatin receptor ligand is contacted with the mammalian cell at a concentration of 1 ng/mL to 1000 ng/mL. The glucocorticoid receptor ligand and the myostatin receptor ligand may be contacted with the mammalian cell simultaneously or at different times.

In particular embodiments, the glucocorticoid receptor ligand may be dexamethasone. The mysostatin receptor ligand, in certain cases, may be GDF8.

A screening method is also provided. In certain embodiments this method comprises: contacting a cell with a candidate agent in the presence of a glucocorticoid receptor ligand an a myostatin receptor ligand, and determining if the candidate agent alters a phenotype of the cell in response to the glucocorticoid receptor ligand and myostatin receptor ligand. In certain embodiments, phenotype may be an atropy response.

The determining may done, in certain cases, by measuring expression gene expression by the cell, e.g., by measuring production of a reporter protein, where the reporter protein is produced using an atrogene promoter-reporter construct, for example. In certain cases, the gene may be an atrogen gene, e.g., MURF-1 or Atrogin-1.

In certain embodiments, the contacting may be done by administering the candidate agent to a mammal and evaluating an atrophy response in muscle tissue of the mammal. In certain cases, the evaluating may comprise measuring gene expression in the muscle tissue and/or measuring muscle mass in the muscle tissue. In particular embodiments, the mammal may be a rat.

In particular embodiments, the contacting may be done by contacting the candidate agent with a cell cultured in vitro, and evaluating an atrophy response by the cultured cell. In this embodiment, the evaluating may comprise measuring gene expression by the cultured cell.

Also provided is a composition comprising a mammalian cell, a glucocorticoid receptor ligand and a myostatin receptor ligand.

DEFINITIONS

Figure 1:
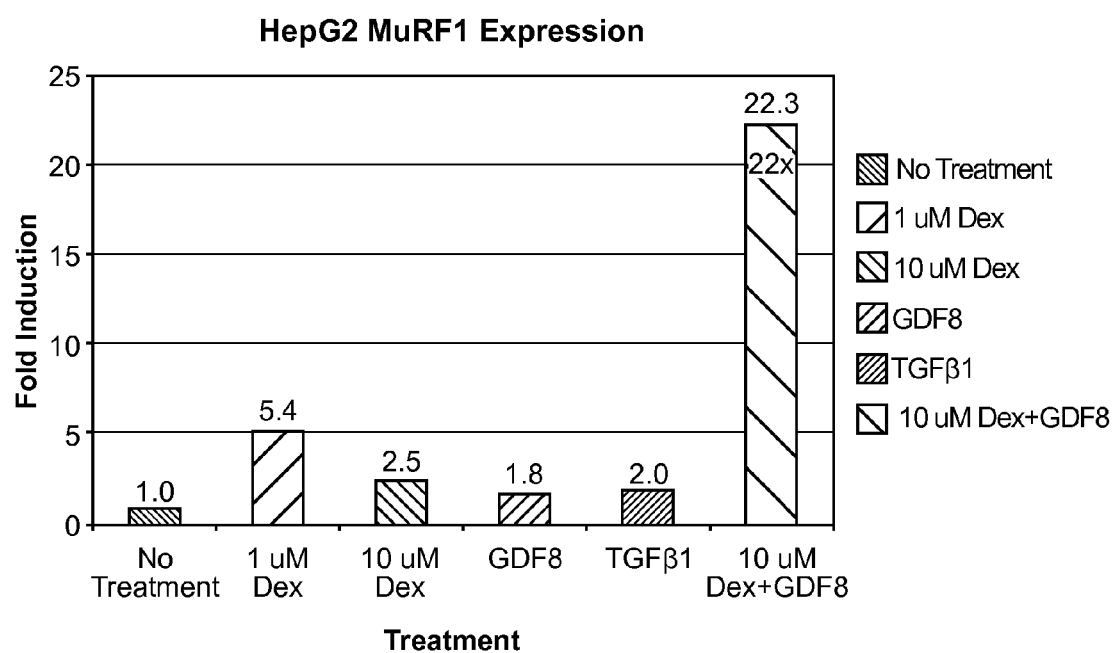
FIG. 1 is a bar graph showing that endogenous MuRF1 expression is synergistically upregulated by Dex and GDF8 treatment in HepG2 cells.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "contacting" means to bring or put together. As such, a first item is contacted with a second item when the two items are brought or put together, e.g., by touching them to each other or combining them in the same solution. Unless otherwise indicated, a cell that is contacted with an agent may be a cell in vivo, i.e., within a multicellular organism, or a cell in vitro, i.e., a cultured cell.

The term "optically detectable protein" refers to a protein whose expression can be detected by the presence of an optical signal produced by the protein. An optical signal is produced by a protein, for example, when the protein is capable of being excited by a particular wavelength of light and emits another wavelength of light which is detectable. An optical signal is produced by a protein, for example, when the protein catalyzes a reaction which results in a light signal. Fluorescent proteins, luminescent proteins, etc., are examples of optically detectable proteins.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

A "non-human" animal refers to any mammal of a species that is not human.

The terms "rodent" and 'rodents' refer to all members of the phylogenetic order Rodentia including any and all progeny of all future generations derived therefrom.

The term "murine" refers to any and all members of the family Muridae, including rats and mice.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an IRES is operably-linked to a coding sequence, the IRES provides for translation of the mRNA transcribed from that coding sequence. "Unlinked" means that the associated genetic elements are not closely associated with one another and the function of one does not affect the other.

The term "luciferase" refers to an enzyme that emits light during the oxidation of its substrate luciferin. The terms luciferin and luciferase do not refer to a particular luciferin or luciferase. They are generic terms for a substrate and its associated enzyme (or protein) that catalyzes a light-producing reaction.

The term "induced" with respect to a promoter, is intended to encompass both the initiation of transcription of a downstream nucleic acid, as well as an increase in the rate of transcription of a downstream nucleic acid that is already being transcribed, compared to an uninduced state.

The term "endogenous" with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

"Treating" or "treatment" of a condition or disease includes providing a clinical benefit to a subject, and includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

The term "candidate agents" means oligonucleotides, polynucleotides, siRNA (which may be administered as a shRNA), gene products, polypeptides, small molecules, e.g., up to 2500 Daltons (Da) in size, and pharmacological compounds that are combined with the cells or the animals described herein to screen for their effect on muscle atrophy. In certain cases, a candidate agent may be delivered as a nucleic acid that is transcribed and/or translated to provide the candidate agent, for example, a RNAi molecule or a polypeptide.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The phrase "muscle cell", as used herein, refers to muscles cells of all kinds, such as including skeletal, smooth and cardiac, precursors of these muscle cells, any intermediate cell existing during the differentiation of a muscle precursor cell, muscle fibers, muscle cell lines, etc. Examples of muscle cells include myoblasts, myotubes, myocytes, cardiac muscle cells, skeletal muscle cells, myofibers etc. A muscle cell may be present in vivo (in an animal) or in vitro (in a cell culture).

The phrase "atrogen gene" refers to a gene whose expression is induced in muscle cells in response to an atrophy-inducing stimulus (e.g., fasting, etc.) prior to a detectable muscle atrophy phenotype, i.e., a detectable loss of muscle mass, shriveling of cells, etc., is observable. MuRF1 and MAFbx, which encode ubiquitin-protein ligases, are examples of atrogen genes, although others exist. The molecular mechanisms that regulate muscle atrophy have been extensively reviewed in, e.g., Siu et al, Front. Biosci. 2009 14:432-52; Murton et al, Biochim. Biophys. Acta 2008 1782:730-43; Tisdale, Curr. Opin. Support Palliat. Care 2007 1:287-92; Zhang et al, Med. Hypotheses. 2007 69:310-21; Cao et al, Int. J. Biochem. Cell Biol. 2005 37:2088-97;

Nader, Int. J. Biochem. Cell Biol. 2005 37:1985-96; Glass, Int. J. Biochem. Cell Biol. 2005 37:1974-84; Du et al, Int. J. Biochem. Cell Biol. 2005 37:2147-55; Franch et al, Curr. Opin. Clin. Nutr. Metab. Care. 2005 8:271-5; Glass, Trends Mol. Med. 2003 9:344-50; and Glass, Nat. Cell Biol. 2003 5:87-90.

The phrase "atrogen promoter" refers a promoter that is induced in muscle cells exposed to an atrophy-inducing stimulus (e.g., fasting, etc) prior to a detectable muscle atrophy phenotype i.e., a detectable loss of muscle mass, shriveling of cells, etc., is observable. An atrogen promoter may be the promoter of a wild type atrogen gene, or an active variant thereof that is, for example, at least 95% identical to a wild type atrogen promoter.

The term "atrophy response" refers to any quantitatively or qualitatively observable muscle atrophy-related response of a cell. An atrophy response may be observable at the molecular level and includes an altered gene expression, e.g., of an endogenous muscle related gene or of a reporter protein driven by a muscle-related promoter such as an atrogen promoter. An atrophy response may also be observable at the cellular level, e.g., by observing an altered cell phenotype such as cell shriveling, cell death or altered cell staining, or at the tissue level, e.g., by observing mass of a muscle, fiber size, cross-sectional area, etc. A decrease in the mass of the muscle is usually accompanied with a weakening of the muscles. An atrophy response may be observed in vitro (in a cultured cell) or in vivo (in an multicellular animal), for example. In an animal, muscle atrophy may be caused by fasting, cachexia, diabetes, dexamethasone treatment, myostatin treatment, being on a ventilator after surgery, muscular dystrophy, sarcopenic frailty of the elderly and amylotrophiic lateral sclerosis, as well as a variety of other muscle-wasting diseases, conditions and treatments.

The term "glucocorticoid receptor", also known as GR, GCR and NR3C1 (nuclear receptor subfamily 3, group C, member 1) is the receptor that cortisol and other glucocorticoids bind to and activates. The glucocorticoid receptor is expressed in almost every cell in the body and regulates genes controlling development, metabolism, and immune response. When the GR binds to a glucorticoid, its primary mechanism of action is the regulation of gene transcription (Lu et al, Pharmacol. Rev. 2006 58: 782-97; Rhen et al, N. Engl. J. Med. 2005 353: 1711-23). The unbound receptor resides in the cytosol of the cell. After the receptor is bound to glucocorticoid, the receptor-glucorticoid complex can take either of two paths. The activated GR complex up-regulates the expression of anti-inflammatory proteins in the nucleus or represses the expression of pro-inflammatory proteins in the cytosol (by preventing the translocation of other transcription factors from the cytosol into the nucleus). The human GR protein and encoding mRNA are provided by Genbank accession nos NP_000167 and NM_000176, respectively. The mouse GR protein and encoding mRNA are provided by Genbank accession nos. NP_03219 and NM_008173, respectively. In the human genome, the GR gene is located on chromosome 5 at 142.64-142.8 M. The glucocorticoid receptor is described in Kumar (Steroids 1999 64: 310-9) and Kumar (J. Steroid Biochem. Mol. Biol.) 2005 94: 383-94, for example. A ligand for the glucocorticoid receptor activates the glucocorticoid receptor. Dexamethasone is an example of a ligand for the glucocorticoid receptor although, as will be discussed below, there are many others.

"GDF8", also known as myostatin (MSTN) or growth differentiation factor 8, is a secreted TGFβ protein family member that inhibits muscle differentiation and growth. Myostatin is produced primarily in skeletal muscle cells, circulates in the blood and acts on muscle tissue, by binding a cell-bound receptor called the Activin type II receptor. The sequence of GDF8 has been determined for a variety of organisms. The human GDF8 protein and encoding mRNA are provided by Genbank accession numbers NP_005250 and NM_005259, respectively. The mouse GDF8 protein and encoding mRNA are provided by Genbank accession numbers NP_034964 and NM_010834, respectively. In the human genome, the GDF8 gene is located on chromosome 2 at 190.63-190.64 Mb. In the mouse genome, the GDF8 gene is located on chromosome 1 at 53.12-53.12 Mb. GDF8 is described in McPherron (Nature 1997 387: 83-90) and Rodgers (Am. J. Physiol. Endocrinol. Metab. 2007 292: E371-2), for example.

The term "myostatin receptor" refers to the receptor through which GDF8 acts. The myostatin receptor is thought to be an activin type II receptor, including the activin IIA receptor (ActRIIA) and activin IIB receptor (ActRIIB) The myostatin receptor is reviewed in Tsuchida et al (Endocr J. 2008 55:11-21), Joulia-Ekaza et al (Curr. Opin. Pharmacol. 2007 7:310-5), Walsh et al (Biochem. Soc. Trans. 2005 33:1513-7) and Tsuchida et al (Immune Endocr. Metabol. Disord. 2004 4:157-66). A ligand for the myostatin receptor activates that receptor. GDF8 is an example of a ligand for the myostatin receptor although, as will be discussed below, there are many others.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, a method that generally comprises contacting a mammalian cell with a glucocorticoid receptor ligand and a myostatin receptor ligand. A screening assay involving the same, is also provided. In the following description the glucocorticoid and myostatin receptor ligands are described first, followed by a description of a method in which those ligands may be employed.

Glucocorticoid Receptor Ligands

The glucocorticoid receptor ligand employed in the subject method may be any compound that binds to and activates the glucocorticoid receptor. The mechanism by which activation of the glucocorticoid receptor initiates downstream response is known. In general terms, upon binding of the ligand to the receptor, the receptor-ligand complex translocates into the cell nucleus, where it binds to glucocorticoid response elements (GRE) in the promoter region of the target genes resulting in the regulation of gene expression. This process is reviewed in, for example, Newton (Thorax 2000 55: 603-13). Activation of the glucocorticoid receptor inhibits the ability of NF-κ B and AP-1 to stimulate transcription (see, e.g., Jonat, Cell 1990 62, 1189; Yang-Yen, Cell 1990 62, 1205; Diamond, Science 1990 249, 1266; and Caldenhoven, Mol. Endocrinol. 1995 9, 401).

A glucocorticoid receptor ligand may be steroidal or non-steroidal. Various exemplary classes of glucocorticoid receptor ligands are described in the following published U.S. patent applications: US20090227548, US20090170898, US20090137655, US20090105292, US20090075995, US20090074675, US20080090792, US20070281959, US20080076795, US20070281928 and US20070149577, which publications are incorporated by reference for disclosure of the glucocorticoid receptor ligands described therein.

In some embodiments, the glucocorticoid receptor ligand may be a glucocorticoid such as dexamethasone, betamethasone, cortisone, hydrocortisone, methylprednisolone, prednisolone, triamcinolone, fludrocortisone acetate, triamcinolone, fluocortolone, clobetasol, diflorasone, mometasone, desoximetasone, including salts, solvates and hydrates thereof. In particular embodiments, the glucocorticoid receptor ligand may have a potency of at least 10 times the potency of hydrocortisone, as reviewed by Begg (Med J. Aust. 1987 146:37-41).

Glucocorticoids and their mechanism of action are reviewed in the following books: Glucocorticoid Hormone: Mechanisms of Action by Y. Sakamoto (Editor) Publisher: Springer-Verlag (June 1986); Glucocorticoid Action: Basic and Clinical Implications (Hardcover) by Tomoshige Kino (Editor), Publisher: New York Academy of Sciences; second edition (Aug. 30, 2004); Glucocorticoids by Goulding (Author) Publisher: Springer/Sci-Tech/Trade; 1 edition (May 11, 2001); and Recent Advances in Glucocorticoid Receptor Action by A. Cato (Editor), Publisher: Springer; 1 edition (Nov. 11, 2002), which are incorporated by reference in their entireties.

Dosages and routes of administration for glucocorticoid receptor ligands are known.

Myostatin Receptor Ligands

The myostatin receptor ligand employed in the subject method may be any compound that binds to and activates the myostatin receptor. Such compounds include peptide and non-peptidic compounds, including GDF8 peptides defined by the following NCBI accession numbers: GI:9506907 (*Rattus norvegicus*), GI:6754752 (*Mus musculus*), GI:4885259 (*Homo sapiens*), GI:48314966 (*Bos Taurus*), GI:260809331 (*Branchiostoma floridae*), GI:51783959 (*Sus scrofa*), GI:47825371 (*Gallus gallus*), GI:18858751 (*Danio rerio*), GI:121583758 (*Macaca mulatta*), GI:50950173 (*Canis lupus familiaris*), GI:120952608 (*Pan troglodytes*), GI:198417205 (*Ciona intestinalis*) and GI:57164247 (*Ovis aries*), including active variants and peptidomimetic variants thereof. The structure of human GDF8 is set forth as MMDB ID: 75808 in NCBI's structure database. In certain cases, a myostatin receptor ligand used herein may have an amino acid sequence that is at least 50% identical to, e.g., at least 60% identical, at least 70% identical, at least 80% identical, at least 85% identical, at least 90% identical, at least 95% identical, or at least 98% identical, to a wild type myostatin receptor ligand.

Assays for identifying myostatin receptor ligands are known and include those described in published U.S. patent applications US20090220491, US20090098114, US20070149458, US20060216279, US20050272028 and US20040248121, which publications are incorporated by reference for disclosure of those assays.

The role of GDF8 in muscle degeneration by activating the myostatin receptor has been reviewed in a variety of publications, including Tsuchida (Expert Opin. Biol. Ther. 2006 6:147-54), Wagner (Curr. Opin. Rheumatol. 2005 17:720-4), Tsuchida (Curr. Drug Targets Immune Endocr. Metabol. Disord. 2004 4:157-66), and Bellinge (Anim. Genet. 2005 36:1-6), which publications are incorporated by reference herein.

Dosages and routes of administration for myostatin receptor ligands are known

Methods

The above-described glucocorticoid receptor ligand and myostatin receptor ligand may be contacted with a mammalian cell in vivo (i.e., by administering the compounds to an animal) or in vitro (i.e., by contacting the compounds with cells grown in culture). The compounds may be contacted with the cell simultaneously (e.g., the compounds may be mixed together prior to contacting the compounds with the cell, or the compounds may be separately combined with the cell at the same time) or at different times. Exemplary in vitro and in vivo methods are described below.

In in vitro methods, the glucocorticoid receptor ligand and myostatin receptor ligand may each be independently contacted with a cultured mammalian cell at a concentration that is consistent with the use of the same compounds individually at a concentration sufficient to effect a response from an isolated cell, as is known in the art. Exemplary effective concentrations and are described in the references cited above as well as many others, and are generally in the range of about 0.1 to 1000 µg/mL, although concentrations outside of this range may be employed in certain circumstances. In general terms, the contacting is done by mixing the compounds with culture medium.

The cultured cell employed in the assay may be any cell that expresses a glucocorticoid receptor and myostatin receptor. If a cell does not express both receptors endogenously, then the receptors may be expressed using recombinant means. Cultured cells from any animal, e.g., cultured mammalian cells, may be employed, including but not limited to: monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci. 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209. In particular embodiments, the cultured cell may be a cultured myocyte, e.g., a cultured cell of skeletal muscle, smooth muscle, or cardiac muscle origin. In exemplary embodiments, the cultured cell may be an HL-1 cell (Claycomb PNAS1998 95: 2979-2984, a BWEM or CLEM cell (Enelmann et al Molecular and Cellular Biochemistry 1996 157), an L6 myoblasts, or a C2C12, SM3, Aza2, BC3H-1, BD1, BD2, BD10, TD33, TD38, TD45, TG1, C2, or AT-1 cell, for example. Methods for culturing such cells are known.

Contacting a cultured cell with the glucocorticoid receptor ligand and myostatin receptor ligand activates the glucocorticoid receptor and the myostatin receptor of the cell, thereby altering a phenotype of the cell. In certain embodiments, the method comprises maintaining the cell in the presence of the compounds for a time sufficient for the cell to exhibit a phenotype that is not produced in the absence of the compounds. In certain cases, the phenotype may be a cell proliferation phenotype, a cell death (apoptosis) phenotype, a change to the cells shape or size, an inflammatory response (observed as an altered production of an inflammatory mediator, for example), an altered staining pattern, or altered gene expression. In particular embodiments, the phenotype may be an atrophy response, as defined above.

In certain cases, the cells may contain a reporter system for evaluating gene expression in the cell. For example, the cell may contain a coding sequence for a reporter protein (e.g., luciferase or GFP), operably linked to a promoter (e.g., a promoter that is induced or repressed during muscle cell development or muscle wasting), where contacting the cell with the compounds induces or represses expression of the reporter protein. In certain embodiments, the promoter may be an atrogen promoter, and contacting the cell with a glucocorticoid receptor ligand and myostatin receptor ligand induces production of the reporter protein. In particular embodiments, the genome of the cell may be may be altered, e.g., by inserting a coding sequence for a reporter protein into an endogenous gene (e.g., an atrogen gene) such that the expression of the reporter is operably linked to the endogenous promoter, or by inserting a recombinant nucleic acid containing both a promoter and reporter-encoding sequence into the genome of the cell.

In in vivo methods, the glucocorticoid receptor ligand and myostatin receptor ligand may be contacted with a mammalian cell by administering the compounds at independent concentrations that are consistent with the use of the same compounds individually at a concentration sufficient to effect a response from the animal, as is known in the art. Exemplary effective concentrations and are described in the references cited above as well as many others, and are generally independently in the range of about 0.01 to 500 milligrams of the compounds per kilogram of animal per dose, e.g., from at least about 0.1 to 100 milligrams agent/kilogram, although concentrations outside of this range may be employed in certain circumstances. In general terms, the contacting is done by administering the compounds to the animal, e.g., orally or by injection (which may be intravenous or intramuscular), locally or systemically. The animal employed in the assay may be any animal, particularly a mammal such as a rodent (e.g., a mouse or rat).

Administering the glucocorticoid receptor ligand and myostatin receptor ligand to the animal activates the glucocorticoid receptor and the myostatin receptor in cells of the animal, thereby altering a phenotype of the animal. In certain embodiments, after the compounds have been administered, the method may comprises maintaining the animal for a time sufficient for the animal to exhibit a phenotype that is not produced in the absence of the compounds. In certain cases, the phenotype may be a cancer-related phenotype (a cell proliferation, cell death, or metastasis-related phenotype) or an inflammatory response-mediated phenotype (e.g., a change in the response of the immune system to a challenge). In particular embodiments, the phenotype may be an atrophy response, as defined above, where in certain embodiments may be observed as an change in muscle mass, a change in muscle cross-section, or a down regulation of myosin synthesis, an activation of a myosin breakdown pathway (e.g., via activation of the ATP-dependent, ubiquitin/proteasome pathway or induction of an E3 ubiquitin ligase).

In certain cases, the cells may contain a recombinant reporter system for evaluating gene expression in the animal. For example, the animal may contain a coding sequence for a reporter protein (e.g., luciferase or GFP), operably linked to a promoter (e.g., a promoter that is induced or repressed during muscle cell development or muscle wasting), where contacting the cell with the compounds induces or represses expression of the reporter protein. In certain embodiments, the promoter may be an atrogen promoter, and administering a glucocorticoid receptor ligand and myostatin receptor ligand to the animal induces production of the reporter protein. In particular embodiments, the genome of the animal may be may be altered, e.g., by inserting a coding sequence for a reporter protein into an endogenous gene (e.g., an atrogen gene) such that the expression of the reporter is operably linked to the endogenous promoter, or by inserting a recombinant nucleic acid containing both a promoter and reporter-encoding sequence into the genome of the cell.

Screening Assays

The above-described method may be employed in a screening assay to identify an agent that modulates the phenotype induced by the glucocorticoid receptor ligand and myostatin receptor ligand. In particular embodiments, the method may be employed to identify an agent that modulates the initiation of muscle cell atrophy. In exemplary embodiments, the method involves contacting a subject cell (i.e., a cell contacted with the glucocorticoid receptor ligand and myostatin receptor ligand, which cell can be present in vitro or in vivo) with a candidate agent, and determining the effect, if any, of the candidate agent on the phenotype induced by the glucocorticoid receptor ligand and myostatin receptor ligand. In a particular embodiment, the phenotype may be assessed by evaluating the production of a reporter protein. In some embodiments, the method involves contacting a cell (in vivo or in vitro) with a candidate agent in the presence of a glucocorticoid receptor ligand an a myostatin receptor ligand; and determining if the candidate agent alters the phenotype of the cell, where the phenotype is produced in response to the glucocorticoid receptor ligand and myostatin receptor ligand.

The term "agent" as used herein describes any molecule, e.g. protein or non-protein organic or inorganic pharmaceutical. Agents of particular interest are those that inhibit initiation of muscle cell atrophy. A plurality of assays is run in parallel with different agent concentrations to obtain a differential response to the various concentrations. One of these concentrations may serve as a negative control, i.e. at zero concentration or below the level of detection.

The terms "candidate agent", "test agent", "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 Da. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design.

Agents that modulate a phenotype may decrease the phenotype by at least 10%, at least 20%, at least 30%, at least 40%, at least 50%, at least 60%, at least 70%, at least 80%, or at least 90%, or more, relative to a control that has not been exposed to the agent.

Agents that modulate the phenotype may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity, etc.

In a particular embodiment, an in vitro method for identifying agents that modulate initiation of muscle cell atrophy is provided. This method generally involves contacting a cultured cell that produces a reporter protein upon initiation of muscle cell atrophy with a candidate agent in the presence of a glucocorticoid receptor ligand an a myostatin receptor ligand; and determining if the candidate agent decreases the production of the reporter protein by the cell as compared to a control cell not treated with the candidate agent.

The cell may be contacted with the glucocorticoid receptor ligand an a myostatin receptor ligand prior to, after or simultaneous with contacting the cell with a candidate agent.

The production of reporter protein(s) may be monitored at different points before and after subjecting the cells to conditions that induce the phenotype. Similarly, the effect of a candidate agent may be determined by measuring the phenotype at several time points. For example, the production of reporter protein(s) may be measured 5 mins, 30 mins, 1 hr, 2 hrs, 4 hrs, 8 hrs, 12 hrs, 24 hrs, 36 hrs, 48 hrs, 72 hrs, 120 hrs, 1 week, 2 week, and up to 1 month, after contacting the cell with a candidate agent.

An in vivo screening assay for identifying agents that modulate initiation of muscle cell atrophy is provided. This method generally involves administering to an animal that produces a reporter protein upon initiation of muscle cell atrophy: a candidate agent, a glucocorticoid receptor ligand and a myostatin receptor ligand; and determining if the candidate agent decreases the production of the reporter protein by the animal as compared to a control animal to which the candidate agent has not been administered.

Any phenotype produced in the in vivo system be monitored at different points before and after administering the candidate agent to the animal. For example, the effect of a candidate agent may be determined by measuring the reporter proteins at several time points. For example, the production of reporter protein(s) may be measured at time 0 hrs, 12 hrs, 24 hrs, 36 hrs, 48 hrs, 72 hrs, 120 hrs, 1 week, 2 week, 1 month, 2 months, 3 months, 5 months, etc., after contacting the cell with a candidate agent. In certain embodiments, the measurement of the reporter proteins may be complimented by measuring the expression of the atrogen gene(s), as well as measuring cell/fiber size, morphology, muscle strength, etc.

Any agent identified by above-described method may be further tested in an animal model. For example, in one embodiment, an animal may be subjected to an atrophy inducing stimuli and contacted with a candidate agent. A number of conditions known to induce atrophy may be used as an atrophy. In an animal, muscle cell atrophy may be initiated by a number of stimuli including but not limited to fasting, ageing, diabetes, advanced cancer, renal failure, sepsis, cachexia, arthritis, osteoporosis, diabetes, denervation, immobilization, muscle unloading, spinal cord injury, glucocorticoid treatment, and the like. In vitro, muscle cell atrophy may be initiated by starving, exposure of cells to for example, glucocorticoids, or to viruses.

Also provided is a composition comprising a mammalian cell, a glucocorticoid receptor ligand and a myostatin receptor ligand. The cell and ligands that may be present in the composition are discussed in greater detail above.

Utility

The in vivo and in vitro assays presented herein provide for methods to identify and test agents that modulate a variety of phenotypes, including those that decrease muscle cell atrophy. These agents may be used in formulations that may be used to treat subjects with muscle cell atrophy. In addition, these agents may be given prophylactically to subjects at risk for developing muscle cell atrophy, e.g., prior to a surgery in which the patient will be put on a ventilator. A subject that may benefit from an agent identified by the methods provided herein may have or be at risk for developing muscle cell atrophy caused by a variety of stimuli. These stimuli include but are not limited to fasting, ageing, advanced cancer, renal failure, sepsis, cachexia, arthritis, osteoporosis, and diabetes. Atrophy of muscles may also be a result of their disuse or denervation, e.g., immobilization, muscle unloading, spinal cord injury, etc. In certain embodiments, the subject may have a health problem that is exacerbated by muscle cell atrophy, such as, HIV, chronic heart failure, chronic kidney disease, liver cirrhosis, burn injuries, osteoporosis, arthritis, etc. The methods of using cells and animal models to screen for candidate compounds that inhibit muscle cell atrophy may be used identify agents that improve protein content, fiber diameter, force production, and fatigue resistance of muscles in subjects with muscle cell atrophy.

EXAMPLES

The following examples are provided in order to demonstrate and further illustrate certain embodiments and aspects of the present invention and are not to be construed as limiting the scope thereof.

Example 1

Cultured HepG2 cells were exposed to 1 µM dexamethasone, 10 µM dexamethasone, 100 ng/ml GDF8, 100 ng/ml TGFβ1, and 10 µM dexamethasone+100 ng/ml GDF8, and expression of endogenous MuRF1 was evaluated by RT-PCR using Taqman RT-PCR assay. Results are shown in FIG. 1. Endogenous MuRF1 was induced 22× over the no treatment control. 10 µM dexamethasone induced expression of endogenous MuRF1 2.5× over the no treatment control, and 100 ng/ml GDF8 induced expression of endogenous MuRF1 1.8× over the no treatment control. Since treatment with a combination of both dexamethasone and GDF8 caused an induction of MuRF1 that is well above the induction of MuRF1 by dexamethasone and GDF8 individually, endogenous MuRF1 expression is synergistically upregulated by dexamethasone and GDF8.

Figure 2:
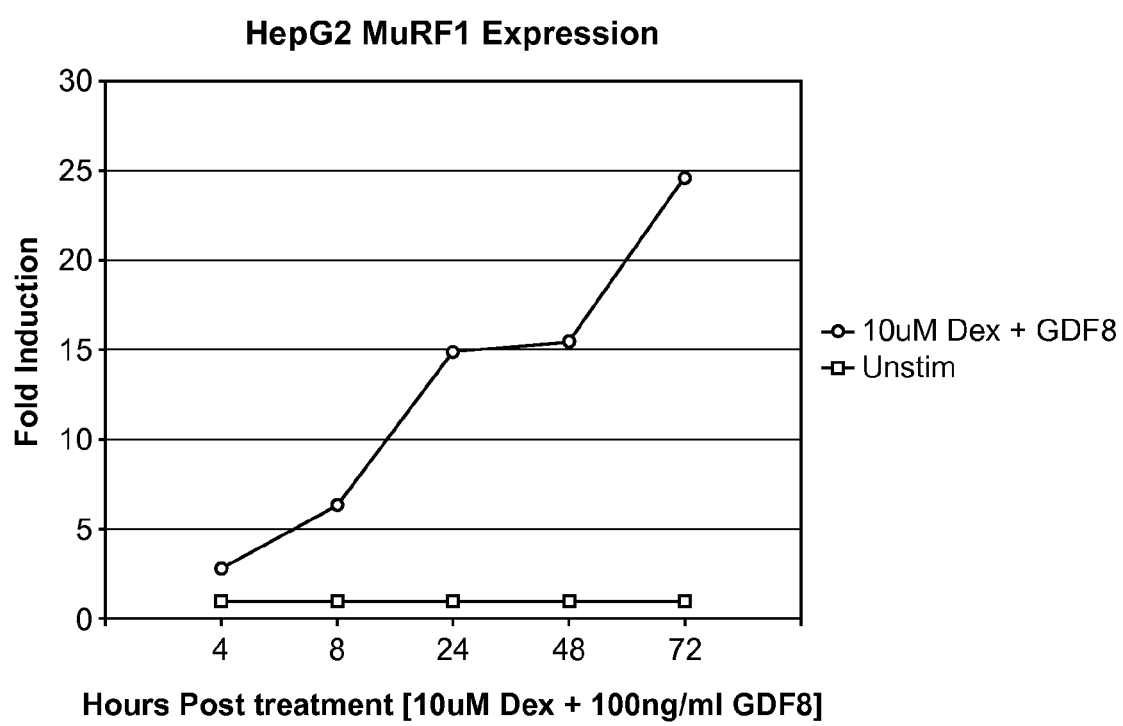
FIG. 2 is a graph showing that MuRF1 mRNA in HepG2 cells is induced within 4 hours of treatment with Dex and GDF8.

FIG. 2 shows a time course of MuRF1 induction after a HepG2 cell is treated with both 10 µM dexamethasone and 100 ng/ml GDF8. MuRF1 induction is observable at four hours of treatment, as compared to controls.

What is claimed is:

1. A method comprising:
   contacting a mammalian cell comprising a glucocorticoid receptor, a myostatin receptor and a recombinant nucleic acid comprising an atrogen promoter that is at least 95% identical to a wild type MURF-1 or MAFbx promoter and operably linked to a coding sequence encoding a reporter protein, with a ligand that activates the glucocorticoid receptor and a ligand that is at least 90% identical to a wild-type mammalian GDF8 and activates the myostatin receptor, thereby activating said atrogen promoter and inducing expression of said reporter protein.

2. The method of claim 1, wherein said contacting initiates an atrophy response by said mammalian cell.

3. The method of claim 1, wherein said contacting is done by contacting said ligand that activates the glucocorticoid receptor and said ligand that activates the myostatin receptor with a cultured cell in vitro.

4. The method of claim 3, wherein said ligand that activates the glucocorticoid receptor is contacted with said mammalian cell at a concentration in the range of 0.1 µM to 100 µM.

5. The method of claim 3, wherein said ligand that activates the myostatin receptor is contacted with said mammalian cell at a concentration of 1 ng/mL to 1000 ng/mL.

6. The method of claim 1, wherein said contacting is done by administering said ligand that activates the glucocorticoid receptor and said ligand that activates the myostatin receptor to a mammal.

7. The method of claim 1, wherein said ligand that activates the glucocorticoid receptor and said ligand that activates the myostatin receptor are contacted with said mammalian cell simultaneously.

8. The method of claim 1, wherein said ligand that activates the glucocorticoid receptor and said ligand that activates the myostatin receptor are contacted with said mammalian cell at different times.

9. The method of claim 1, wherein said ligand that activates the glucocorticoid receptor is dexamethasone.

10. The method of claim 1, wherein said ligand that activates the myostatin receptor comprises an amino acid sequence that is at least 95% identical to a wild-type GDF8.

11. The method of claim 1, wherein said ligand that activates the myostatin receptor is GDF8.

12. The method of claim 1, wherein said atrogen promoter is identical to a wild type MURF-1 or MAFbx promoter.

13. The method of claim 1, wherein the contacting is done in the presence of a candidate agent; and the method further comprises measuring production of the reporter protein.

14. The method of claim 13, wherein the method further comprises determining if said candidate agent alters cell phenotype of said cell.

15. The method of claim 14, wherein said cell phenotype is a muscle atrophy phenotype.

16. The method of claim 13, wherein said contacting is done by contacting said candidate agent with a cultured cell in vitro; and the method further comprises determining a muscle atrophy phenotype in the cultured cell.

17. The method claim 13, wherein said contacting is done by administering said candidate agent to a mammal; and the method further comprises determining a muscle atrophy phenotype in muscle tissue of the mammal.

18. The method of claim 17, wherein said determining a muscle atrophy phenotype comprises measuring muscle mass.

19. The method of claim 17, wherein said mammal is a rat.

20. The method of claim 13, wherein said candidate agent is a siRNA.

* * * * *